(12) United States Patent
Matschke

(10) Patent No.: US 6,228,327 B1
(45) Date of Patent: May 8, 2001

(54) APPARATUS AND METHOD FOR SIMULTANEOUSLY GERMICIDALLY CLEANSING AIR AND WATER

(75) Inventor: Arthur L. Matschke, Brookfield Center, CT (US)

(73) Assignee: MolecuCare, Inc., Brookfield, CT (US)

( * ) Notice: Subject to any disclaimer, the term of this patent is extended or adjusted under 35 U.S.C. 154(b) by 0 days.

(21) Appl. No.: 09/499,597

(22) Filed: Feb. 7, 2000

Related U.S. Application Data

(63) Continuation-in-part of application No. 09/112,500, filed on Jul. 9, 1998, now Pat. No. 6,022,511.

(51) Int. Cl.$^7$ ........................................................ A61L 9/20
(52) U.S. Cl. ..................... 422/121; 250/436; 422/24
(58) Field of Search ................ 422/121, 24; 250/455.11, 250/436

(56) References Cited

U.S. PATENT DOCUMENTS

| | | |
|---|---|---|
| 3,798,879 | 3/1974 | Schmidt-Burbach et al. . |
| 4,201,916 | 5/1980 | Ellner . |
| 4,661,264 | 4/1987 | Goudy, Jr. . |
| 4,739,152 | 4/1988 | Downs . |
| 4,786,812 | 11/1988 | Humphreys . |
| 4,798,702 | 1/1989 | Tucker . |
| 4,877,964 | 10/1989 | Tanaka et al. . |
| 5,107,687 | 4/1992 | Candeloro . |
| 5,120,450 | 6/1992 | Stanley, Jr. . |
| 5,200,156 | 4/1993 | Wedekamo . |
| 5,219,534 | 6/1993 | Reynolds . |
| 5,247,178 | 9/1993 | Ury et al. . |
| 5,330,722 | 7/1994 | Pick et al. . |
| 5,417,852 | 5/1995 | Furness, Jr. et al. . |
| 5,497,573 | 3/1996 | Stadjuhar et al. . |
| 5,523,057 | 6/1996 | Mazzilli . |
| 5,612,001 | 3/1997 | Matschke . |
| 5,635,133 | 6/1997 | Glazman . |
| 5,874,741 | 2/1999 | Matschke . |
| 6,022,511 | 2/2000 | Matschke . |

*Primary Examiner*—Krissane Thornton
(74) *Attorney, Agent, or Firm*—Bazerman & Drangel, PC

(57) ABSTRACT

A germicidal UV chamber for use on air passing through a duct system, such as a central air system which replace one or more sections of the duct and, in essence, becomes part of the duct work. Each chamber is in the form of one or more ellipsoid sections which focus the energy uniformly throughout the chamber also positioned in the chamber is an ultraviolet transparent conduit through which a liquid such as water passes and is also germicidally cleansed.

17 Claims, 3 Drawing Sheets

APPARATUS AND METHOD FOR SIMULTANEOUSLY GERMICIDALLY CLEANSING AIR AND WATER

This application is a continuation-in-part of previously filed application Ser. No. 09/112,500 filed Jul. 9, 1998 to be issued on Feb. 8, 2000 as U.S. Pat. No. 6,022,511.

BACKGROUND OF THE INVENTION

Airborne bacteria or other microorganisms permeate the air we breath and the water we drink. Some of these microorganisms with which we share our environment cause disease. Medical environments, such as hospitals, have a high degree of pathogens in the air and water and highly susceptible, weakened patients. The existence of biological weapons of mass destruction require protection of command centers, barracks, ships, and other closed environments against biological agents. Today's modem sealed high-rise structures with central air conditioning and heating, through duct systems, need protection from the spread of disease among its occupants and from colonies of microorganisms which may live in the duct and water system. Today, biologic protection is necessary on the battlefield and in the workplace, the hospital and the home.

Much effort has gone into trying to destroy atmospheric pathogens with only limited success. It has long been recognized that pathogens can be destroyed in the air if they are irradiated with ultraviolet (UV) light at a wavelength of 253.7 nanometers (Germicidal Wavelength). In order for the UV light to kill microorganisms, the UV rays must directly strike the microorganisms for a sufficient time. Because of the absolute necessity for antiseptic surroundings, UV lamps of the required Germicidal Wavelength are often used in operating rooms, wards, and nurseries of hospitals.

The exposure to UV light necessary to kill microorganisms is a product of time and intensity. However, due to the dangers to humans of irradiation from wide-spread use of UV lamps, exposure to UV light has been limited by government regulations. The current occupant exposure limit (ACGIH, NIOSH standard) for 254 m ultraviolet germicidal wavelength ceiling fixtures is 6000 $\mu$watts seconds/cm$^2$ in one eight hour day. Thus, the maximum allowed intensity per second is 0.2 $\mu$W/cm$^2$. At this intensity, eight hours at the allowed exposure level is required to gain a 90% kill of *Mycobacterium tuberculosis* (90% kill-value 6200 $\mu$watts/cm$^2$) at head height. For 100% kill using the same standard, the value is 10,000 $\mu$watts/cm$^2$, requiring 13.89 hours of exposure. The required low intensity, and resulting long exposure times, permit migration of microorganisms out of range of the UV lamp and result in accumulation of microorganisms which survive the UV lamp in the room. Increasing air circulation does not increase exposure of microorganisms. It only moves organisms past the UV lamp without sufficient exposure.

To overcome these problems there have been various attempts to circulate air passed UV sources in enclosures which acts to shield the UV irradiation from the room's occupant. Usually, such systems are free-standing, or wall or ceiling mounted devices which circulate the air in a single room through the enclosure and, accordingly, whose protection is confined to that room. See, for example, U.S. Pat. No. 5,330,722 to Pick, which discloses a germicidal air purifier which draws air through a chamber in which there is mounted an ultraviolet source which acts to kill microorganisms caught in the filter structure. Similarly, U.S. Pat. No. 5,612,001 to Arthur L. Matschke, discloses a germicidal air cleansing enclosure having an internal ellipsoid chamber which contains UV lamps along the major axis of the ellipsoid. The unit is free-standing and treats air in a single room.

While a system such as that disclosed in U.S. Pat. No. 5,612,001 to Arthur L. Matschke, may be highly effective to cleans the contents of a single room, normal air conditioning and heating ducts would continue to allow circulation of untreated air into and out of a room. This allows untreated air containing pathogens from another room, or in the duct system, to enter the room and come into contact with humans before being treated and allow a certain amount of pathogens in a room to enter the duct system prior to being treated by the free-standing unit.

Various attempts have been made to place ultraviolet light sources in duct systems to germicidally cleans fluids such as air as they pass through the duct system. See, for example, U.S. Pat. No. 5,635,133 to Glazman, U.S. Pat. No. 5,200,156 to Wedekamp and U.S. Pat. No. 5,107,687 to Candeloro. Each of these patents disclose an ultraviolet irradiation source in a duct to cleanse a fluid traveling through a duct of uniform diameter. The UV source is at right angles to the duct walls and UV energy is directed at least in part along the path of fluid flow. Thus, the level of ultraviolet energy varies along the flow path. As a result, the air circulated past the UV lamps in the prior art receive an uneven distribution of ultraviolet energy and a rapid diminution of energy levels outside the immediate area of the UV source. The parent of the present patent application, now U.S. Pat. No. 6,022,511, to Matschke, discloses an ellipsoidal, ultraviolet reflective chamber mounted in a duct system which exposes the air passing through the chamber to sufficient UV energy to germicidally cleanse all of such air. However, it does not provide the means for treating water in the same closed environment.

Bacteria or other microorganisms not only permeate the air we breath but also the water we drink. Much effort has gone into trying to limit or destroy water-borne pathogens. It has long been recognized that pathogens can also be destroyed in water if they are irradiated with ultraviolet (UV) light of a wavelength of 253.7 nanometers. In order for the UV light to kill microorganisms, and particularly pathogens, the rays must directly strike them. U.S. Pat. No. 5,874,741 to Matschke discloses an ellipsoid, ultraviolet reflective chamber to expose water passing through the chamber to sufficient UV energy to germicidally cleanse all of such water.

SUMMARY OF THE PRESENT INVENTION

It is an object of the present invention to provide an ultraviolet chamber for simultaneous processing of air and water which combines both optics and air and water flow techniques to kill microorganisms present in the air and water.

It is a further object of the present invention to cause all air and water flowing throughout the present invention to be exposed at a uniform constant rate of high levels of ultraviolet radiation.

It is a further object of the present invention to do so with no ultraviolet exposure to humans.

The present invention is a germicidal chamber which uniformly irradiates all of the air passing through a duct system in which it is mounted, such as a central air system. The chamber replaces one or more sections of the duct and, in essence, becomes part of the duct work. The chamber has running along the chamber's longitudinal axis an ultraviolet transparent pipe through which water or other fluid may pass. The ultraviolet transparent pipe is attached at both ends of the ultraviolet chamber to conventional pipes which passe through the wall of the duct and form part of the fluid circulatory system, such as a buildings water supply.

Each chamber is in the form of one or more ellipsoid sections which focus the energy uniformly throughout the chamber. A sphere is a form of ellipsoid and can be used in carrying forward the present operation. The chamber is connected to the duct so that all air drawn into the duct system must pass through the chamber. To accomplish this, each chamber is integral with the duct forcing all of the air in the duct on the upstream side to pass through the chamber. Such a system allows a chamber to be mounted at each return vent to cleanse the air from a room as it returns to the duct system. In addition, where exterior contamination is feared, such as in a germ warfare situation, outside air entering the system may also be treated.

Chambers may be connected by their respective ducts in series or in parallel. A single chamber may be formed from a series of ellipsoids in order to allow intense uniform irradiation over an extended distance in relatively narrow duct-work, thereby substantially increasing the exposure per unit of power consumption.

Similarity, the germicidally cleansed water can be introduced into a building or structures plumbing so that the only water circulated in the system will have passed through an ultraviolet chamber.

A combined air water chamber of this type is not only highly useful in structure such as hospitals, office towers, homes, anti-germ warfare structures and the like, but is useful in any closed environment where a large number of people are situated in relative proximity such on airplanes or buses. In such environments, the present invention not only protects against infection but reduces the amount of water to be carried and thus the amount of dead weight to be carried.

DESCRIPTION OF THE PREFERRED EMBODIMENT

Figure 1:
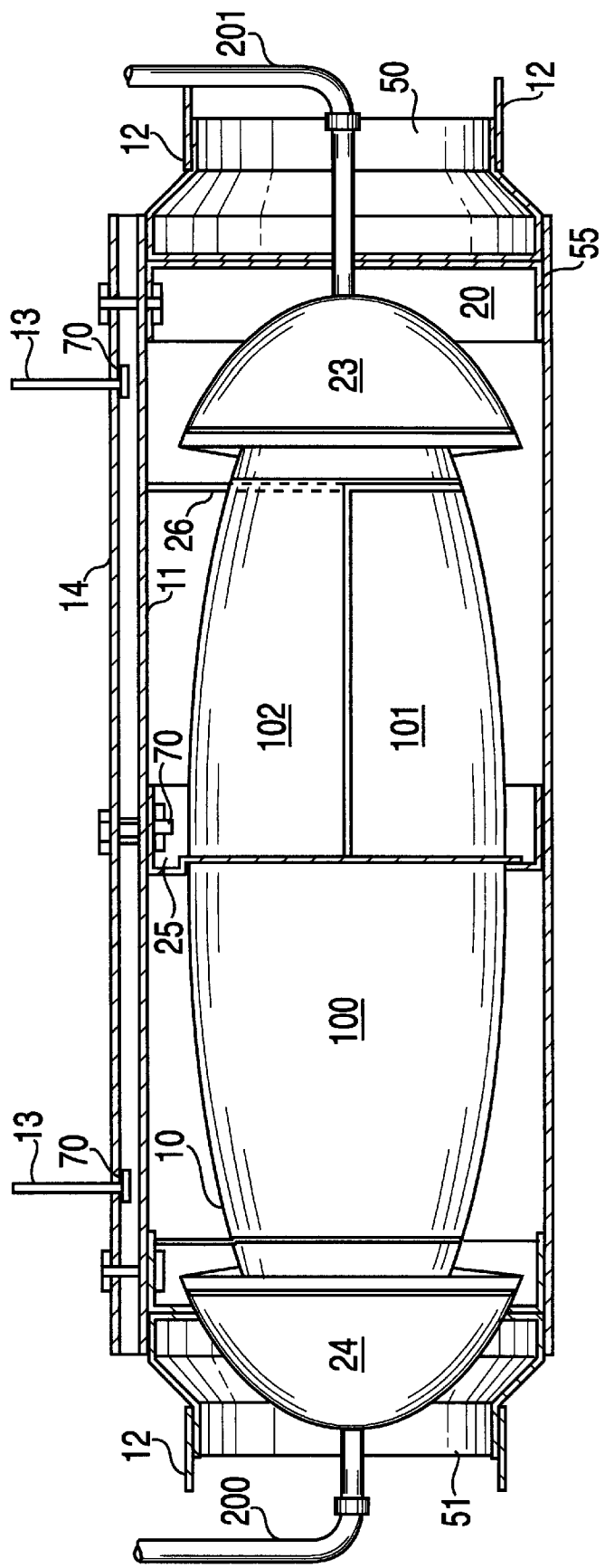
FIG. 1 is a partial cut-away front view of a chamber, in accordance with the present invention, with the shell wall partially removed.

In the present invention, the duct work of a central air system is modified to replace a portion of the duct with an ellipsoidal UV chamber 10 which becomes part of the central air duct system. Air is normally circulated through the central air system including through the chamber 10 by the HVAC fan.

The germicidal cleansing chamber 10 is mounted within a shell 11 connected to an air duct 12. The shell 11 can be used to insulate the chamber from extremes of temperature and provide alternatives for finishes to give the chamber 10 an appearance that will allow it to be hung under the ceiling. The shell 11 has mounted on it mounting spine 14. The spine 14 is of sufficient cross-section and strength to carry the chamber 10 and may be U-shaped to allow positioning and proper mounting of the shell 11. The spine 14, and thus shell 11 and germicidal cleansing chamber 10, are mounted to the ceiling by conventional mounting means such as suspension rods, cables or straps 13. Each of the suspension means 13 are attached to mounting spine 14 by conventional means such as nut 70.

At either end of the elliptical central portion 16 of chamber 10 are end caps 23 and 24. The central portion 16 of chamber 10 may be composed of a number of sections 101, 102, and 103 to allow access into the interior of chamber 10. The central portion 16 and the end caps 23 and 24 may be made from spun aluminum or be formed from a molded material having aluminum or other highly UV reflective material deposited on the interior.

Figure 2:
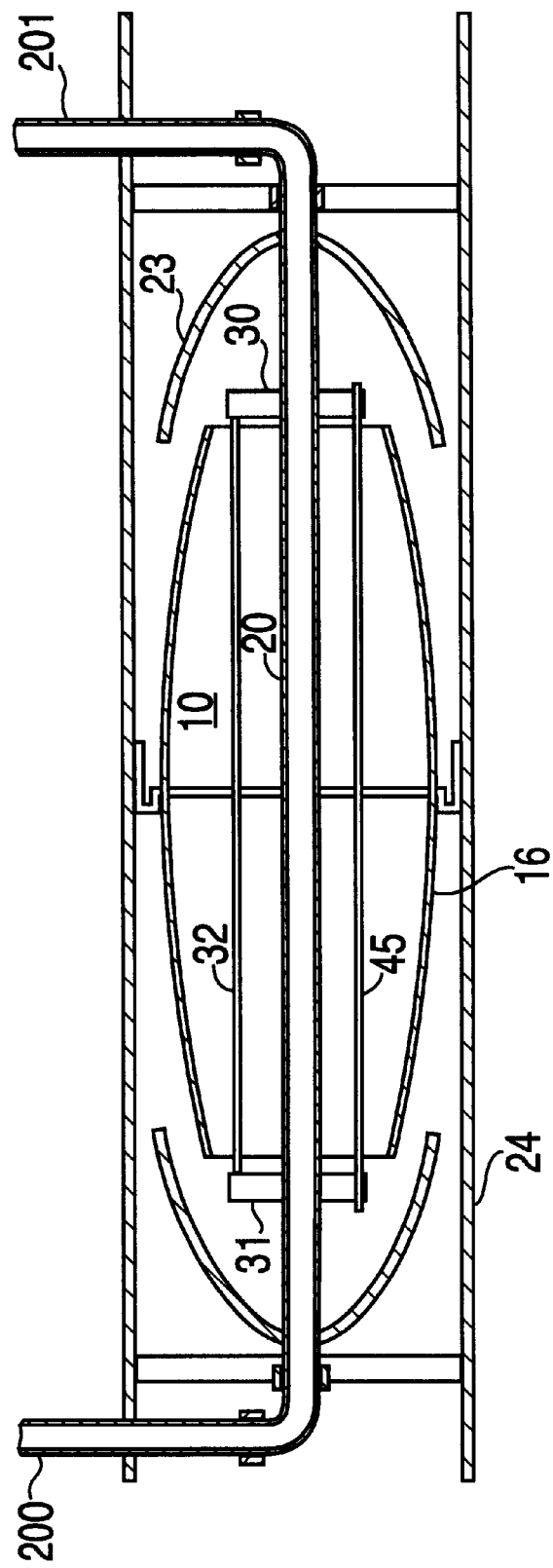
FIG. 2 is a cross-sectional view of the chamber FIG. 1.

The central portion 16 of chamber 10 is an ellipsoid. The end caps 23 and 24 are displaced paraboloids which share loci with the elliptical chamber. Normally, when mounted in a duct, it will be in the form of an elongated chamber as seen in FIGS. 1 and 2. However, the ellipsoid may be as sphere.

The bulkhead 25 is in sealed engagement with both the shell 11 and the central portion 16 of chamber 10 at the mid-point of central position 16. As air is drawn into the duct system, it will be pass through chamber 10, entering in the space between the end cap 23 and central portion 16. Since the chamber 10 can be mounted in existing duct systems, the air will be drawn into the chamber 10 by the circulation system of the duct system, such as a building HVAC fan.

Mounted in the chamber 10 are mounting rings 30 and 31 between which UV light sources 32 are positioned. Also attached to the mounting rings 30 and 31 are positioning rods 45 which hold the mounting rings 30 and 31 in their respective positions. For clarity of the drawings, only one UV light source 32 and one positioning rod 45 is shown. The number of UV light source s will be determined by the overall requirements of the system. The mounting rings 30 and 31 include an interior circuit board (not shown) protected by the structure of the mounting rings 30 and 31 from UV irradiation.

The chamber may be simply located in an existing duct system at a return vent or elsewhere. Adapters 50 and 51 on either side of shell 11 mate the chamber to a duct system preferably at or near a return air register.

Passing down the center of the chamber 10 is a UV transparent conduit 20. Conduit 20 is connected by conventional means to conventional inlet pipe 200 and outlet 201. Water or other fluids to be germicidally cleansed flow from inlet pipe 200 through chamber 10 and out outlet pipe 201. The direction of flow can be reversed without effecting the cleansing efficiency. Pipes 200 and 201 pass through the duct walls 12 and are attached to the water distribution system. The water distribution system should be of such a design that only treated water can leave the pipes for use. The conduit 20 is shown positioned between end caps 23, 24. Alternatively, the UV transparent conduit 20 may enter and leave the chamber 10 through its central position 16.

Because of the elliptical configuration of the body portion in conjunction with the effect of the parabolic end caps, the UV light generated by the UV light source is evenly dispersed throughout the extended length of the chamber 10. Any point in the chamber 10 receives the same quantity of UV light in all directions as any other point within the chamber 10. The formation of the walls of the chamber 10 by spinning and the qualities of aluminum from which it is spun, acts to ensure the greatest part of the energy generated by the UV light sources 32 is reflected back into the chamber 10 rather than being absorbed by the walls of the chamber. The effect of UV irradiation on a micro-organism is dependent on both UV intensity and length of time of exposure to the UV irradiation. Since the walls are highly reflective, the irradiation intensity created reaches a steady state which is substantially greater than the output of the lamps and, because of the configuration, is evenly distributed through the chamber.

Figure 3:
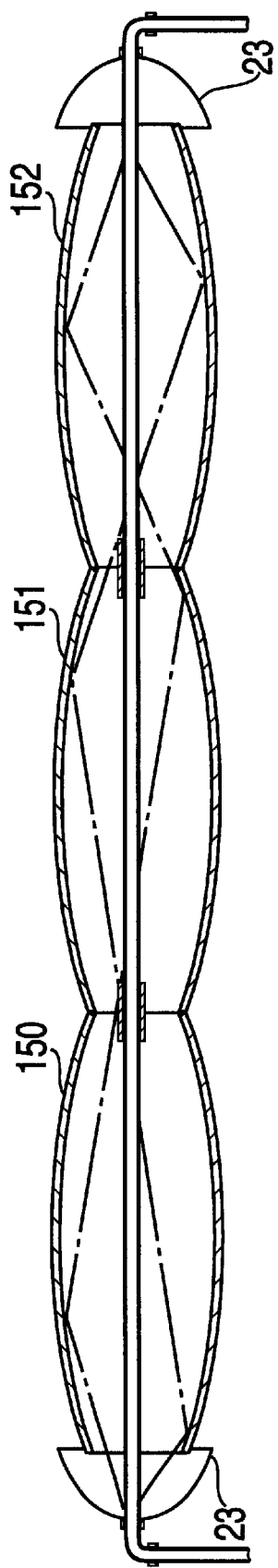
FIG. 3 is a schematic diagram showing the path of light along a multi-ellipsoid chamber.

FIGS. 3 show a further embodiment of the invention. Given that the irradiation is evenly distributed throughout the chamber, the percentage of microorganisms destroyed would be dependent on the intensity of the irradiation and the residence time for an individual microorganism to pass through the chamber. Thus, extending the length of the chamber increases exposure at a given UV irradiation level. On the other hand, duct works are relatively narrow and places physical limits on the width of a chamber 10. In the embodiment of FIG. 3 two or more truncated elliptical sections are combined to extend the exposure time of a microorganism at a constant irradiation level, as more fully discussed below.

The chamber 10 is formed from truncated elliptical sections 150–152 which are symmetrical and mate at corresponding points along their axis. A greater number of sections may be used and each ellipsoidal section may be formed from one or more sub-sections. Where sections 150–152 meet, they form intersection openings sufficient to allow both the fluid and UV irradiation to pass between the sections, the first such section having an inlet opening to allow the fluid to enter the chamber and the last such ellipsoidal element having an exit opening to allow the fluid to exit the chamber. It is contemplated that the sections 150-152 will intersect in a plane at right angle to the principle axis of the sections 150–152. If so, the intersection opening will be in the form of a circle. The radius of the intersection opening should be equal to or less than 0.16 times the distance of the total chamber ellipsoid length (l) plus the diameter of the ellipsoid section at its widest point (d), i.e. Radius$\leq$0.16 (l+d), to gain full advantage of the present invention. However the plane of intersection of the intersection may not be at right angles to the principal axis of sections 101 and 102. In such cases, the sections 101 and 102 could meet at an angle, allowing chamber 10 to be positioned around objects and/or to conform to the available space. The resulting intersection would be an ellipse or an ovate.

While the invention has been described as having a preferred design, it is understood that it is capable of further modification, uses and/or adaptations of the invention following in general principle of the invention and including such departures from the present disclosure as come within known or customary practice in the art to which the invention pertains, as may be applied to the central figures hereinabove set forth and fall within the scope of the invention of the limits of the appended claims.

I claim:

1. An apparatus for germicidally cleansing air and a fluid comprising:

a chamber positioned in a duct system having an inlet opening to allow air to enter the chamber and a separate exit opening to allow air to exit the chamber;

said chamber having a UV transparent conduit passing through at least a portion of its length with first openings to allow a fluid to enter the chamber and second openings to allow a fluid to leave the chamber;

an ultraviolet light source positioned in the chamber;

the internal walls of the chamber being made from an ultraviolet reflective material and the walls of the chamber shaped to direct ultraviolet light into and upon the walls of the chamber uniformly throughout the chamber and such that the energy in the chamber accumulates over time to reach a uniform steady state energy level greater than that emitted by the UV source; and an adapter to mate the chamber with the duct system.

2. An apparatus according to claim 1, wherein the chamber is an ellipsoid.

3. An apparatus according to claim 2, wherein the ellipsoid chamber is a sphere.

4. An apparatus according to claim 1, wherein the chamber is formed from more than one truncated ellipsoidal section.

5. An apparatus according to claim 4, wherein the truncated ellipsoidal sections intersect to form a circular opening having a radius of equal to or less than 0.16 of the sum of an untruncated ellipsoidal length and the ellipsoidal diameter of the section at its widest point.

6. An apparatus according to claim 4, wherein interconnected truncated mating ellipsoidal sections are aligned along the same axis.

7. An apparatus according to claim 4, wherein the interconnected truncated mating ellipsoidal sections meet at an angle.

8. An apparatus according to claim 1, wherein UV reflective end caps are positioned at the inlet opening and the exit opening of the chamber to reflect UV irradiation back into the chamber.

9. An apparatus according to claim 8, wherein the end caps form a seal with the ducts so that all air passing through the ducts must pass through the chamber.

10. An apparatus for germicidally cleansing two fluids comprising:

a chamber positioned in a duct system having an inlet opening to allow a first fluid to enter the chamber and a separate exit opening to allow that fluid to exit the chamber;

said chamber also having an ultraviolet transparent conduit having a first opening to allow a second fluid to enter the conduit, travel along a length of the conduit and a second opening to allow that fluid to leave the conduit;

an ultraviolet light source positioned in the chamber;

the internal walls of the chamber being made from ultraviolet reflective material and the walls of the chamber shaped to direct ultraviolet light into and upon the walls of the chamber and uniformly throughout the chamber such that the energy in the chamber accumulates over time to reach a uniform steady state energy level greater than that emitted by the ultraviolet light source.

11. An apparatus according to claim 10, wherein the chamber is an ellipsoid.

12. An apparatus according to claim 11, wherein the ellipsoid chamber is a sphere.

13. An apparatus according to claim 10, wherein the chamber is formed from more than one truncated ellipsoidal section.

14. An apparatus according to claim 13, wherein the truncated ellipsoidal sections intersect to form a circular opening having a radius of equal to or less than 0.16 of the sum of an untruncated ellipsoidal length and the ellipsoidal diameter of the section at its widest point.

15. An apparatus according to claim 13, wherein interconnected truncated mating ellipsoidal sections are aligned along the same axis.

16. An apparatus according to claim 13, wherein interconnected truncated mating ellipsoidal sections meet at an angle.

17. An apparatus according to claim 10, wherein UV reflective end caps are positioned at the inlet opening and the exit opening of the chamber to reflect UV irradiation back into the chamber.

* * * * *